(12) United States Patent
Himmelsbach et al.

(10) Patent No.: US 7,183,280 B2
(45) Date of Patent: Feb. 27, 2007

(54) BICYCLIC IMIDAZOLE DERIVATIVES, THE PREPARATION THEREOF AND THEIR USE AS PHARMACEUTICAL COMPOSITIONS

(75) Inventors: Frank Himmelsbach, Mittelbiberach (DE); Elke Langkopf, Warthausen (DE); Matthias Eckhardt, Biberach (DE); Norbert Hauel, Schemmerhofen (DE); Mohammad Tadayyon, Ulm (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/018,894

(22) Filed: Dec. 21, 2004

(65) Prior Publication Data

US 2005/0143377 A1  Jun. 30, 2005

Related U.S. Application Data

(60) Provisional application No. 60/538,684, filed on Jan. 23, 2004.

(51) Int. Cl.
*A61K 31/5025* (2006.01)
*A61K 31/519* (2006.01)
*C07D 487/04* (2006.01)

(52) U.S. Cl. ...................... 514/248; 544/236
(58) Field of Classification Search ............... 544/236; 514/248
See application file for complete search history.

(56) References Cited

U.S. PATENT DOCUMENTS 7,074,798 B2 * 7/2006 Yoshikawa et al. ...... 514/263.2

| | | | |
|---|---|---|---|
| 2002/0198205 A1 | 12/2002 | Himmelsbach et al. |
| 2004/0097510 A1 | 5/2004 | Himmelsbach et al. |
| 2004/0116328 A1 | 6/2004 | Yoshikawa et al. |
| 2004/0138214 A1 | 7/2004 | Himmelsbach et al. |
| 2005/0020574 A1 | 1/2005 | Hauel et al. |
| 2005/0026921 A1 | 2/2005 | Eckhardt et al. |

FOREIGN PATENT DOCUMENTS

| WO | WO 02/068420 A1 | 9/2002 |
| WO | WO 03/104229 A1 | 12/2003 |
| WO | WO 2004/018468 A2 | 3/2004 |
| WO | WO 2004/041820 A1 | 5/2004 |
| WO | WO 2004/050658 A1 | 6/2004 |
| WO | WO 2004/111051 A1 | 12/2004 |

* cited by examiner

*Primary Examiner*—Joseph K. McKane
*Assistant Examiner*—Michael P. Barker
(74) *Attorney, Agent, or Firm*—Thomas Blankinship; Mary-Ellen M. Devlin; Michael Morris

(57) ABSTRACT

The present invention relates to bicyclic imidazole compounds of general formula

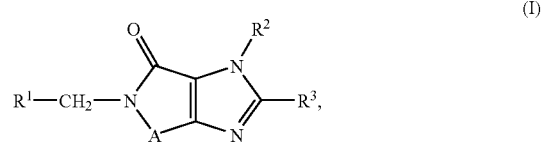

(I)

wherein $R^1$ to $R^3$ and A are defined as in claims 1 to 8, the tautomers, the enantiomers, the stereoisomers, the mixtures thereof and the salts thereof, which have valuable pharmacological properties, particularly an inhibiting effect on the activity of the enzyme dipeptidylpeptidase-IV (DPP-IV).

14 Claims, No Drawings

BICYCLIC IMIDAZOLE DERIVATIVES, THE PREPARATION THEREOF AND THEIR USE AS PHARMACEUTICAL COMPOSITIONS

This application claims benefit of U.S. Ser. No. 60/538,684, dated Jan. 23, 2004, and claims priority to Federal Republic of Germany Application Nos. DE 103 60 835.4, dated Dec. 23, 2003, and DE 102004046530.4, dated Sep. 24, 2004 each of which is incorporated by reference in its entirety.

The present invention relates to new bicyclic imidazole compounds of general formula

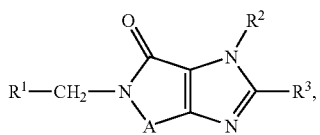

the tautomers, the enantiomers, the stereoisomers, the mixtures thereof and the salts thereof, particularly the physiologically acceptable salts thereof with inorganic or organic acids which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

In the above formula I
$R^1$ denotes a pyridinyl, phenylpyridinyl, (pyridinylphenyl)carbonyl, quinolinyl, phenylquinolinyl, isoquinolinyl, phenylisoquinolinyl or phenanthridinyl group substituted by the groups $R^{10}$ to $R^{12}$, while the nitrogen atom of the above-mentioned groups is substituted by an oxygen atom, and
$R^{10}$ denotes a hydrogen atom, a fluorine, chlorine, bromine or iodine atom,
a $C_{1-4}$-alkyl, hydroxy or $C_{1-4}$-alkyloxy group,
a nitro, amino, $C_{1-3}$-alkylamino, di-($C_{1-3}$-alkyl)amino, pyrrolidin-1-yl, piperidin-1-yl or morpholin-4-yl group,
a $C_{1-3}$-alkyl-carbonylamino or N—($C_{1-3}$-alkyl)-$C_{1-3}$-alkyl-carbonylamino group,
a $C_{1-3}$-alkylsulphonylamino or N—($C_{1-3}$-alkyl)-$C_{1-3}$-alkyl-sulphonylamino group,
a $C_{1-3}$-alkyl-carbonyl group,
a cyano, aminocarbonyl, ($C_{1-3}$-alkylamino)carbonyl, [di-($C_{1-3}$-alkyl)-amino]carbonyl, pyrrolidin-1-ylcarbonyl, piperidin-1-ylcarbonyl or morpholin-4-ylcarbonyl group,
a methyl or methoxy group substituted by 1 to 3 fluorine atoms,
a $C_{1-3}$-alkylsulphanyl, $C_{1-3}$-alkylsulphinyl or $C_{1-3}$-alkylsulphonyl group,
a $C_{2-4}$-alkenyl or $C_{2-4}$-alkynyl group,
a $C_{3-4}$-alkenyloxy or $C_{3-4}$-alkynyloxy group,
a $C_{3-6}$-cycloalkyl or $C_{3-6}$-cycloalkyloxy group,
a $C_{3-6}$-cycloalkyl-$C_{1-3}$-alkyl or $C_{3-6}$-cycloalkyl-$C_{1-3}$-alkyloxy group or
an aryl, aryloxy, aryl-$C_{1-3}$-alkyl or aryl-$C_{1-3}$-alkyloxy group,
$R^{11}$ and $R^{12}$, which may be identical or different, represent a hydrogen atom, a fluorine, chlorine or bromine atom or a methyl, difluoromethyl, trifluoromethyl, methoxy, difluoromethoxy, trifluoromethoxy or cyano group,
or a pyridazinyl, phenylpyridazinyl, (pyridazinylphenyl)carbonyl, pyrimidinyl, phenylpyrimidinyl, (pyrimidinylphenyl)carbonyl, pyrazinyl, phenylpyrazinyl, (pyrazinylphenyl)carbonyl, quinolinyl, phenylquinolinyl, quinazolinyl, phenylquinazolinyl, phthalazinyl, phenylphthalazinyl, quinoxalinyl, phenylquinoxalinyl, naphthyridinyl or phenylnaphthyridinyl group substituted by the groups $R^{10}$ to $R^{12}$, while at least one nitrogen atom of the above-mentioned groups is substituted by an oxygen atom, and $R^{10}$ to $R^{12}$ are as hereinbefore defined,
$R^2$ denotes a 2-methyl-2-propen-1-yl, 2-chloro-2-propen-1-yl or 3-bromo-2-propen-1-yl group,
a 1-buten-1-yl, 3-methyl-1-buten-1-yl, 3-methyl-2-buten-1-yl, 2-buten-1-yl, 2-methyl-2-buten-1-yl or 2,3-dimethyl-2-buten-1-yl group,
a 2-butyn-1-yl group,
a 1-cyclopenten-1-ylmethyl group or
a benzyl, 2-fluorobenzyl, 2-chlorobenzyl, 2-bromobenzyl or 2-cyanobenzyl group,
$R^3$ denotes a 3-aminopiperidin-1-yl, 3-amino-azepan-1-yl, piperazin-1-yl or [1,4]-diazepan-1-yl group
or an amino group substituted by the groups $R^4$ and $R^5$ wherein
$R^4$ denotes a methyl or ethyl group and
$R^5$ denotes a 2-aminoethyl group, while the ethyl moiety of the 2-aminoethyl group may be substituted by one or two methyl groups,
and A denotes a —CO—N($R^6$)— group, while the nitrogen atom of this group is linked to the imidazo ring of general formula I, and
$R^6$ denotes a hydrogen atom, a $C_{1-4}$-alkyl, $C_{3-6}$-cycloalkyl or aryl group,
a —CH=CH— group substituted by $R^6$, where $R^6$ is as hereinbefore defined,
a —C($R^7$)=N— group, where the nitrogen atom of this group is linked to the imidazo ring of general formula I, and
$R^7$ denotes a hydrogen atom, a $C_{1-4}$-alkyl, $C_{3-6}$-cycloalkyl or aryl group,
or an —N=C($R^7$) group, while the carbon atom of this group is linked to the imidazo ring of general formula I, and $R^7$ is as hereinbefore defined,
while by the aryl groups mentioned in the definition of the above groups is meant a phenyl group substituted by $R^{10}$ and $R^{11}$ and $R^{10}$ and $R^{11}$ are as hereinbefore defined,
and the above-mentioned alkyl and alkenyl groups may be straight-chain or branched,
the tautomers, the enantiomers, the diastereomers, the mixtures thereof and the salts thereof.

Preferred compounds of general formula I are those wherein
$R^1$ denotes a pyridinyl, phenylpyridinyl, (pyridinylphenyl)carbonyl, quinolinyl, phenylquinolinyl, isoquinolinyl, phenylisoquinolinyl or phenanthridinyl group substituted by the groups $R^{10}$ and $R^{11}$, while the nitrogen atom of the above-mentioned groups is substituted by an oxygen atom, and
$R^{10}$ and $R^{11}$, which may be identical or different, denote a hydrogen atom, a fluorine, chlorine or bromine atom or a methyl, difluoromethyl, trifluoromethyl, methoxy, difluoromethoxy, trifluoromethoxy or cyano group, or a pyrimidinyl, phenylpyrimidinyl, (pyrimidinylphenyl) carbonyl, quinazolinyl, phenylquinazolinyl, quinoxalinyl, phenylquinoxalinyl or naphthyridinyl group substituted by the groups $R^{10}$ and $R^{11}$, while at least one nitrogen atom of the above-mentioned groups is substituted by an oxygen atom, and $R^{10}$ and $R^{11}$ are as hereinbefore defined, $R^2$ denotes a 2-butyn-1-yl group, $R^3$ denotes a 3-aminopiperidin-1-yl, piperazin-1-yl or [1,4]-diazepan-1-yl group, or an amino group substituted by the groups $R^4$ and $R^5$ wherein
  $R^4$ denotes a methyl or ethyl group and
  $R^5$ denotes a 2-aminoethyl group, while the ethyl moiety of the 2-aminoethyl group may be substituted by one or two methyl groups, and A denotes a —CO—N($R^6$) group, while the nitrogen atom of this group is linked to the imidazo ring of general formula I, and
  $R^6$ denotes a methyl, ethyl, propyl, isopropyl, cyclopropyl or phenyl group, or an —N=C($R^7$)— group, while the carbon atom of this group is linked to the imidazo ring of general formula I, and
  $R^7$ denotes a hydrogen atom or a methyl group, the tautomers, the enantiomers, the diastereomers, the mixtures thereof and the salts thereof.

Particularly preferred are those compounds of general formula I wherein $R^7$ denotes a phenylpyridinyl, quinolinyl, isoquinolinyl or phenanthridinyl group substituted by the groups $R^{10}$ and $R^{11}$, while the nitrogen atom of the above-mentioned groups is substituted by an oxygen atom, and
  $R^{10}$ denotes a hydrogen atom or a methyl, methoxy or cyano group and
  $R^{11}$ denotes a hydrogen atom or a methyl group, or a phenylpyrimidinyl, quinazolinyl, quinoxalinyl or naphthyridinyl group substituted by the groups $R^{10}$ and $R^{11}$, while at least one nitrogen atom of the above-mentioned groups is substituted by an oxygen atom, and $R^{10}$ and $R^{11}$ are as hereinbefore defined, $R^2$ denotes a 2-butyn-1-yl group, $R^3$ denotes a 3-aminopiperidin-1-yl, piperazin-1-yl or [1,4]-diazepan-1-yl group, or an amino group substituted by the groups $R^4$ and $R^5$ wherein
  $R^4$ denotes a methyl group and
  $R^5$ denotes a 2-aminoethyl group, while the ethyl moiety of the 2-aminoethyl group may be substituted by one or two methyl groups, and A denotes a —CO—N($R^6$)— group, while the nitrogen atom of this group is linked to the imidazo ring of general formula I, and
  $R^6$ denotes a methyl, ethyl, isopropyl, cyclopropyl or phenyl group, or a —N=C($R^7$)— group, while the carbon atom of this group is linked to the imidazo ring of general formula I, and
  $R^7$ denotes a hydrogen atom or a methyl group, the tautomers, the enantiomers, the diastereomers, the mixtures thereof and the salts thereof.

A first sub-group comprises those compounds of the above formula I wherein $R^1$, $R^2$ and A are as hereinbefore defined and $R^3$ denotes a 3-aminopiperidin-1-yl group, the tautomers, the enantiomers, the diastereomers, the mixtures thereof and the salts thereof.

A second sub-group comprises those compounds of the above formula I wherein $R^1$, $R^2$ and A are as hereinbefore defined and $R^3$ denotes a piperazin-1-yl group, the tautomers, the enantiomers, the diastereomers, the mixtures thereof and the salts thereof.

A third sub-group comprises those compounds of the above formula I wherein $R^1$, $R^2$ and A are as hereinbefore defined and $R^3$ denotes a [1,4]-diazepan-1-yl group, the tautomers, the enantiomers, the diastereomers, the mixtures thereof and the salts thereof.

Most particularly preferred are those compounds of general formula I wherein $R^1$ denotes a quinolinyl, isoquinolinyl, methylisoquinolinyl or phenanthridinyl group, while the nitrogen atom of the above-mentioned groups is substituted by an oxygen atom, a quinazolinyl or methylquinazolinyl group, while the nitrogen atom of the above-mentioned groups is substituted by an oxygen atom, or a quinoxalinyl group wherein both nitrogen atoms are substituted by oxygen atoms, $R^2$ denotes a 2-butyn-1-yl group, $R^3$ denotes a 3-aminopiperidin-1-yl or a piperazin-1-yl group and A denotes a —CO—N($R^6$)— group, while the nitrogen atom of this group is linked to the imidazo ring of general formula I, and $R^6$ denotes a methyl group, or a —N=C($R^7$)-group, while the carbon atom of this group is linked to the imidazo ring of general formula I, and $R^7$ denotes a hydrogen atom, the tautomers, the enantiomers, the diastereomers, the mixtures thereof and the salts thereof;

particular mention should be made of the following compounds of general formula I:

(a) 1-[(4-methyl-3-oxy-quinazolin-2-yl)methyl]-3-methyl-7-(2-butyn-1-yl)-8-((R)-3-amino-piperidin-1-yl)-xanthine, (b) 1-[(1-oxy-quinolin-2-yl)methyl]-3-methyl-7-(2-butyn-1-yl)-8-((R)-3-amino-piperidin-1-yl)-xanthine, (c) 1-[(3-methyl-2-oxy-isoquinolin-1-yl)methyl]-3-methyl-7-(2-butyn-1-yl)-8-((R)-3-amino-piperidin-1-yl)-xanthine, (d) 1-[(5-oxy-phenanthridin-6-yl)methyl]-3-methyl-7-(2-butyn-1-yl)-8-((R)-3-amino-piperidin-1-yl)-xanthine, (e) 1-[(3-oxy-quinazolin-2-yl)methyl]-3-methyl-7-(2-butyn-1-yl)-8-((R)-3-amino-piperidin-1-yl)-xanthine, (f) 2-((R)-3-amino-piperidin-1-yl)-3-(2-butyn-1-yl)-5-[(1-oxy-quinolin-2-yl)methyl)]-3,5-dihydro-imidazo[4,5-d]pyridazin-4-one, (g) 2-((R)-3-amino-piperidin-1-yl)-3-(2-butyn-1-yl)-5-[(3-oxy-quinazolin-2-yl)methyl]-3,5-dihydro-imidazo[4,5-d]pyridazin-4-one, (h) 2-(piperazin-1-yl )-3-(2-butyn-1-yl)-5-[(4-methyl-3-oxy-quinazolin-2-yl)methyl]-3,5-dihydro-imidazo[4,5-d]pyridazin-4-one, (i) 2-((R)-3-amino-piperidin-1-yl)-3-(2-butyn-1-yl)-5-[(4-methyl-3-oxy-quinazolin-2-yl)methyl]-3,5-dihydro-imidazo[4,5-d]pyridazin-4-one, (j)1-[(2-oxy-isoquinolin-3-yl)methyl]-3-methyl-7-(2-butyn-1-yl)-8-((R)-3 -amino-piperidin-1-yl)-xanthine and (k) 2-((R)-3-amino-piperidin-1-yl)-3-(2-butyn-1-yl)-5-(2-oxy-isoquinolin-3-yl)methyl]-3,5-dihydro-imidazo[4,5-d]pyridazin-4-one as well as the tautomers, enantiomers, diastereomers, mixtures thereof and the salts thereof.

According to the invention the compounds of general formula I are obtained by methods known per se, for example by the following methods:

a) reacting a compound of general formula

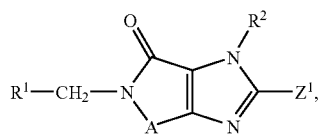

(II)

wherein

R$^1$, R$^2$ and A are as hereinbefore defined and

Z$^1$ denotes a leaving group such as a halogen atom, a substituted hydroxy, mercapto, sulphinyl, sulphonyl or sulphonyloxy group such as a chlorine or bromine atom, a methanesulphonyl or methanesulphonyloxy group, with R$^3$—H, the enantiomers or the salts thereof, where R$^3$ is as hereinbefore defined.

The reaction is expediently carried out in a solvent such as isopropanol, butanol, tetrahydrofuran, dioxane, dimethylformamide, dimethylsulphoxide, ethyleneglycol monomethylether, ethyleneglycol diethylether, N-methyl-pyrrolidin-2-one or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium-based catalyst at temperatures between −20 and 180° C., but preferably at temperatures between −10 and 120° C. The reaction may, however, also be carried out without solvent or in an excess of the amino compound R$^3$—H.

b) deprotecting a compound of general formula

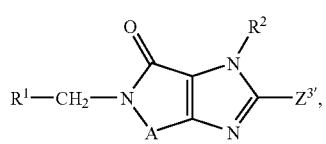

(III)

wherein R$^1$, R$^2$ and A are as hereinbefore defined and R$^{3\prime}$ denotes one of the groups given as a definition of R$^3$ hereinbefore, wherein the amino or imino group is protected by a protecting group such as a tert.-butyloxycarbonyl, benzyloxycarbonyl, formyl or trifluoroacetyl group, while for the amino function the phthalyl group is an additional possibility.

The tert.-butyloxycarbonyl group is preferably cleaved by treating with an acid such as trifluoroacetic acid or hydrochloric acid or by treating with bromotrimethylsilane or iodotrimethylsilane, optionally using a solvent such as methylene chloride, ethyl acetate, dioxane, methanol, isopropanol or diethyl ether at temperatures between 0 and 80° C.

However, the benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar.

The formyl and trifluoroacetyl group are cleaved, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide at temperatures between 0 and 120° C., preferably at temperatures between 10 and 100° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

In the reactions described hereinbefore, any reactive groups present such as amino, alkylamino or imino groups may be protected during the reaction by conventional protecting groups which are cleaved again after the reaction.

For example, a protecting group for an amino, alkylamino or imino group may be a formyl, acetyl, trifluoroacetyl, ethoxycarbonyl, tert-butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid optionally with the addition of an acid such as hydrochloric acid at temperatures between 0 and 100° C., but preferably at temperatures between 20 and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethyl ether.

A trifluoroacetyl group is preferably cleaved by treating with an acid such as hydrochloric acid optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula 1 with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae II and III used as starting compounds are either known from the literature or may be prepared by methods known from the literature (see Examples I to X).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2", which appeared in Proc. Natl. Acad. Sci. Vol. 90, pp. 5757–5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by the addition of 30 µl of solubilised Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example no.) | DPP IV inhibition $IC_{50}$ [nM] |
| --- | --- |
| 1 | 2 |
| 1(1) | 1 |
| 1(2) | 4 |
| 1(3) | 6 |
| 1(4) | 2 |

The compounds prepared according to the invention are well tolerated as no toxic side effects could be detected in rats after the oral administration of 10 mg/kg of the compound of Example 1, for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, pre-diabetes, reduced glucose tolerance or changes in the fasting blood sugar, diabetic complications (e.g. retinopathy, nephropathy or neuropathies), metabolic acidosis or ketosis, reactive hypoglycaemia, insulin resistance, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based pancreatic carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Suitable therapeutic agents for such combinations include for example antidiabetic agents such as metformin, sulphonylureas (e.g. glibenclamid, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), PPAR-gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, SGLT2 inhibitors such as T-1095 or KGT-1251(869682), inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or LXRalpha antagonists, LXRbeta agonists or LXRalpha/beta regulators or active substances for the treatment of obesity, such as e.g. sibutramine or tetrahydrolipostatin, dexfenfluramine, axokine, antagonists of the cannabinoid 1 receptor, MCH-1 receptor antagonists, MC4 receptor agonists, NPY5 or NPY2 antagonists or $β_3$-agonists such as SB-418790 or AD-9677 as well as agonists of the $5HT_2c$ receptor.

It is also possible to combine the compounds with drugs for treating high blood pressure such as e.g. AII antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I

1-[(4-Methyl-3-oxy-quinazolin-2-yl)methyl]-3-methyl-7-(2-butyn-1-yl)-8-[(R)-3-(tert.-butyloxycarbonylamino)-piperidin-1-yl-xanthine A mixture of 300 mg of 3-methyl-7-(2-butyn-1-yl)-8-[(R)-3-(tert.-butyloxycarbonyl-amino)-piperidin-1-yl]-xanthine, 151 mg of 2-chloromethyl-4-methyl-quinazoline-3-oxide and 220 mg of potassium carbonate in 50 ml of acetonitrile is heated for seven minutes in the microwave at 170° C. Then the acetonitrile is distilled off and the flask residue is chromatographed through a silica gel column with ethyl acetate/methanol (100:0 to 90:10) as eluant.

Yield: 121 mg (29% of theory)

$R_f$ value: 0.60 (silica gel, ethyl acetate/methanol=9:1)

Mass spectrum (ESI$^+$): m/z=589 [M+H]$^+$

EXAMPLE II

3-Methyl-7-(2-butyn-1-yl)-8-[(R)-3-(tert.-butyloxycarbonylamino)-piperidin-1-yl]-xanthine 11.00 g of (R)-3-tert.-butyloxycarbonylamino-piperidine are added to 15.00 g of 3-methyl-7-(2-butyn-1-yl)-8-bromo-xanthine and 16.00 g of potassium carbonate in 100 ml of dimethylsulphoxide and the thick, light beige suspension is stirred for four hours with a mechanical stirrer at approx. 114° C. Then another 900 mg of (R)-3-tert.-butyloxycarbonylamino-piperidine, dissolved in 10 ml of dimethylsulphoxide, are added to the reaction mixture and this is stirred for a further two hours at 114° C. After cooling to ambient temperature the reaction mixture is diluted with copious amounts of water. The precipitate formed is thoroughly triturated until no more clumps are left, and suction filtered. The light solid is again suspended with water, suction filtered, washed with water and diethyl ether and dried in the circulating air dryer at 60° C.

Yield: 19.73 g (94% of theory)
$R_f$ value: 0.64 (silica gel, ethyl acetate)
Mass spectrum (ESI$^+$): m/z=417 [M+H]$^+$ The following compounds are obtained analogously to Example II:

(1) 2-[(R)-3-(tert.-butyloxycarbonylamino)-piperidin-1-yl]-3-(2-butyn-1-yl)-3,5-dihydro-imidazo[4,5-d]pyridazin-4-one (carried out in N,N-dimethylformamide at 80° C.)
$R_f$ value: 0.55 (silica gel, ethyl acetate)
Mass spectrum (ESI$^+$): m/z=387 [M+H]$^+$

EXAMPLE III 3-methyl-7-(2-butyn-1-yl)-8-bromo-xanthine 17.06 g of 1-bromo-2-butyne are added to 30.17 g of 3-methyl-8-bromo-xanthine and 27.00 ml of Hünig base in 370 ml of N,N-dimethylformamide. The reaction mixture is stirred for two hours at ambient temperature, then another 1 ml of 1-bromo-2-butyne is added and stirring is continued for another hour at ambient temperature. For working up the reaction mixture is diluted with approx. 300 ml of water. The light precipitate formed is suction filtered and washed with water. The filter cake is washed with a little ethanol and diethyl ether and dried in the circulating air dryer at 60° C.

Yield: 30.50 g (84% of theory)
$R_f$ value: 0.24 (silica gel, methylene chloride/methanol=95:5)
Mass spectrum (ESI$^+$): m/z=297, 299 [M+H]$^+$

EXAMPLE IV

1-[(1-oxy-quinolin-2-yl)methyl]-3-methyl-7-(2-butyn-1-yl)-8-[(R)-3-(tert.-butyloxy-carbonylamino)-piperidin-1-yl]-xanthine Prepared by heating 450 mg of 3-methyl-7-(2-butyn-1-yl)-8-[(R)-3-(tert.-butyl-oxycarbonylamino)-piperidin-1-yl]-xanthine, 245 mg of 2-chloromethyl-quinoline-1-oxide and 800 mg of potassium carbonate in 5 ml of N,N-dimethylformamide to 80° C.

Yield: 622 mg (100% of theory)
$R_f$ value: 0.26 (silica gel, ethyl acetate)
Mass spectrum (ESI$^+$): m/z=574 [M+H]$^+$ The following compounds are obtained analogously to Example IV:

(1) 1-[(3-methyl-2-oxy-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.17 (silica gel, ethyl acetate)
Mass spectrum (ESI$^+$): m/z=588 [M+H]$^+$ (2) 1-[(5-oxy-phenanthridin-6-yl)methyl]-3-methyl-7-(2-butyn-1-yl)-8-[(R)-3-(tert.-butyloxycarbonylamino)-piperidin-1-yl]-xanthine
$R_f$ value: 0.47 (silica gel, ethyl acetate)
Mass spectrum (ESI$^+$): m/z=624 [M+H]$^+$ (3) 1-[(3-oxy-quinazolin-2-yl)methyl]-3-methyl-7-(2-butyn-1-yl)-8-[(R)-3-(tert.-butyloxycarbonylamino)-piperidin-1-yl]-xanthine
$R_f$ value: 0.29 (silica gel, ethyl acetate)
Mass spectrum (ESI$^+$): m/z=575 [M+H]$^+$ (4) 1-[(1,4-dioxy-quinoxalin-2-yl)methyl]-3-methyl-7-(2-butyn-1-yl)-8-[(R)-3-(tert.-butyloxycarbonylamino)-piperidin-1-yl]-xanthine
$R_f$ value: 0.53 (silica gel, ethyl acetate)
Mass spectrum (ESI$^+$): m/z=591 [M+H]$^+$ (5) 2-[(R)-3-(tert.-butyloxycarbonylamino)-piperidin-1-yl]-3-(2-butyn-1-yl)-5-[(1-oxy-quinolin-2-yl)methyl)]-3,5-dihydro-imidazo[4,5-d]pyridazin-4-one
Mass spectrum (ESI$^+$): m/z=544 [M+H]$^+$ (6) 2-[(R)-3-(tert.-butyloxycarbonylamino)-piperidin-1-yl]-3-(2-butyn-1-yl)-5-[(3-methyl-2-oxy-isoquinolin-1-yl)methyl]-3,5-dihydro-imidazo[4,5-d]pyridazin-4-one
Mass spectrum (ESI$^+$): m/z=558 [M+H]$^+$ (7) 2-[(R)-3-(tert.-butyloxycarbonylamino)-piperidin-1-yl]-3-(2-butyn-1-yl)-5-[(5-oxy-phenanthridin-6-yl)methyl]-3,5-dihydro-imidazo[4,5-d]pyridazin-4-one
Mass spectrum (ESI$^+$): m/z=594 [M+H]$^+$ (8) 2-[(R)-3-(tert.-butyloxycarbonylamino)-piperidin-1-yl]-3-(2-butyn-1-yl)-5-[(3-oxy-quinazolin-2-yl)methyl]-3,5-dihydro-imidazo[4,5-d]pyridazin-4-one
Mass spectrum (ESI$^+$): m/z=545 [M+H]$^+$ (9) 2-[(R)-3-(tert.-butyloxycarbonylamino)-piperidin-1-yl]-3-(2-butyn-1-yl)-5-[(1,4-dioxy-quinoxalin-2-yl)methyl]-3,5-dihydro-imidazo[4,5-d]pyridazin-4-one
Mass spectrum (ESI$^+$): m/z=561 [M+H]+

(10) 2-bromo-3-(2-butyn-1-yl)-5-[(4-methyl-3-oxy-quinazolin-2-yl)methyl]-3,5-dihydro-imidazo[4,5-d]pyridazin-4-one
$R_f$ value: 0.30 (silica gel, ethyl acetate)
Mass spectrum (ESI$^+$): m/z=439, 441 [M+H]+

(11) 2-[(R)-3-(tert.-butyloxycarbonylamino)-piperidin-1-yl]-3-(2-butyn-1-yl)-5-[(4-methyl-3-oxy-quinazolin-2-yl)methyl]-3,5-dihydro-imidazo[4,5-d]pyridazin-4-one
$R_f$ value: 0.40 (silica gel, ethyl acetate/methanol=9:1)
Mass spectrum (ESI$^+$): m/z=559 [M+H]$^+$

(12) 1-[(2-oxy-isoquinolin-3-yl)methyl]-3-methyl-7-(2-butyn-1-yl)-8-[(R)-3-(tert.-butyl-oxycarbonylamino)-piperidin-1-yl]-xanthine
$R_f$ value: 0.35 (silica gel, methylene chloride/methanol=95:5)
Mass spectrum (ESI$^+$): m/z=574 [M+H]$^+$

(13) 2-[(R)-3-(tert.-butyloxycarbonylamino)-piperidin-1-yl]-3-(2-butyn-1-yl)-5 -(2-oxy-isoquinolin-3-yl)methyl]-3,5-dihydro-imidazo[4,5-d]pyridazin-4-one
$R_f$ value: 0.10 (silica gel, ethyl acetate/methanol=98:2)
Mass spectrum (ESI$^+$): m/z=544 [M+H]$^+$

EXAMPLE V

1-Chloromethyl-3-methyl-isoquinoline-2-oxide

A solution of 300 mg of 1-chloromethyl-3-methyl-isoquinoline in 3 ml of methylene chloride is combined with 390 mg of 3-chloroperoxybenzoic acid and stirred overnight at ambient temperature. The reaction mixture is diluted with some methylene chloride and extracted with saturated sodium hydrogen carbonate solution. The combined organic phases are dried over magnesium sulphate and evaporated down. The solid, yellowish crude product is triturated with tert.-butylmethylether, suction filtered, washed with tert.-butylmethylether and dried.

Yield: 285 mg (88% of theory)
$R_f$ value: 0.31 (silica gel, ethyl acetate/petroleum ether=3: 2)
Mass spectrum (ESI$^+$): m/z=208, 210 [M+H]$^+$ The following compound is obtained analogously to Example V:

(1) 6-chloromethyl-phenanthridine-5-oxide $R_f$ value: 0.66 (silica gel, ethyl acetate/petroleum ether=3:2)

Mass spectrum (ESI$^+$): m/z=244, 246 [M+H]$^+$

EXAMPLE VI 2-bromomethyl-quinazoline-3-oxide

A solution of 1.00 g of 2-methyl-quinazoline-3-oxide in 30 ml of glacial acetic acid is combined dropwise with a solution of 0.48 ml of bromine in 10 ml of glacial acetic acid and stirred overnight at ambient temperature. Then the reaction mixture is stirred for another two hours at 80° C. The glacial acetic acid is largely distilled off and the residue is stirred with saturated sodium hydrogen carbonate solution. The lumpy precipitate formed is taken up in ethyl acetate. The ethyl acetate is distilled off again and the fine precipitate is suction filtered, washed with ethanol and tert.-butyl-methylether and dried. The crude product is purified by chromatography through a silica gel column with ethyl acetate as eluant.

Yield: 654 mg (44% of theory)
$R_f$ value: 0.52 (silica gel, ethyl acetate)
Mass spectrum (ESI$^+$): m/z=239, 241 [M+H]$^+$

EXAMPLE VII 2-bromo-3-(2-butyn-1-yl)-3,5-dihydro-imidazo[4,5-d]pyridazin-4-one 0.31 ml of hydrazine hydrate (99%), dissolved in 1 ml of ethanol, are added dropwise at ambient temperature to a solution of 1.80 g of methyl 2-bromo-3-(2-butyn-1-yl)-5-formyl-3H-imidazole-4-carboxylate in 25 ml of ethanol. Five minutes later 1.5 ml of concentrated acetic acid are added and the mixture is refluxed for 30 minutes. After cooling the precipitated solid is suction filtered, washed with 10 ml of ethanol and 20 ml of diethyl ether and dried.

Yield: 1.25 g of (74% of theory)
Mass spectrum (ESI$^+$): m/z=267, 269 [M+H]+
1H-NMR spectrum (d6-DMSO): δ=1.80 (s, 3H); 5.28 (s, 2H); 8.38 (s, 1H); 12.99 (s, 1H) ppm

EXAMPLE VIII

Methyl 2-bromo-3-(2-butyn-1-yl)-5-formyl-3H-imidazole-4-carboxylate 43 ml of a 1 M solution of diisobutyl-aluminium hydride in tetrahydrofuran are added dropwise to a solution of 13.5 g of dimethyl 2-bromo-1-(2-butyn-1-yl)-1H-imidazole-4,5-dicarboxylate in 220 ml of tetrahydrofuran under an argon atmosphere at −70° C. within 20 minutes. The mixture is stirred for a further four hours at −70° C., then 20 ml of a mixture of 1 M hydrochloric acid and tetrahydrofuran are added dropwise. After heating to ambient temperature approx. 200 ml of water are added and the mixture is extracted three times with 70 ml of ethyl acetate. The combined extracts are dried and evaporated down. The crude product thus obtained is purified by column chromatography through silica gel with petroleum ether/ethyl acetate (80:20 to 50:50) as eluant.

Yield: 6.40 g (52% of theory)
Mass spectrum (ESI$^+$): m/z=285, 287 [M+H]$^+$
1H-NMR spectrum (d6-DMSO): δ=1.80 (s, 3H); 3.93 (s, 3H); 5.11 (s, 2H); 10.12 (s, 1H) ppm

EXAMPLE IX

Dimethyl 2-bromo-1-(2-butyn-1-yl)-1H-imidazole-4,5-dicarboxylate

A solution of 15.0 g of dimethyl 2-bromo-imidazole-4,5-dicarboxylate, 5.15 ml of 1-bromo-2-butyne and 50 ml of N,N-diisopropylethylamine in 280 ml of tetrahydrofuran is refluxed for one hour. The mixture is concentrated by evaporation, the residue is combined with approx. 100 ml of water and extracted three times with 70 ml of ethyl acetate. The extracts are washed with 50 ml of water, dried and evaporated down. The crude product thus obtained is purified by column chromatography through silica gel using methylene chloride/ethanol (100:0 to 98:2) as eluant.

Yield: 13.50 g (75% of theory)
$R_f$ value: 0.82 (silica gel, methylene chloride/ethanol=9:1)
Mass spectrum (ESI$^+$): m/z=315, 317 [M+H]$^+$

EXAMPLE X 3-chloromethyl-isoquinoline-2-oxide

Prepared by treating 3-chloromethyl-isoquinoline with 35% hydrogen peroxide solution in glacial acetic acid at 70° C.

$R_f$ value: 0.30 (silica gel, ethyl acetate/methanol=98:2)
Mass spectrum (ESI$^+$): m/z=194, 196 [M+H]$^+$ Preparation of the final compounds:

EXAMPLE 1

1-[(4-methyl-3-oxy-quinazolin-2-yl)methyl]-3-methyl-7-(2-butyn-1-yl)-8-((R)-3-amino-piperidin-1-yl)-xanthine

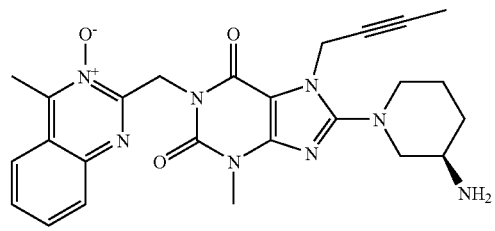

A mixture of 121 mg of 1-[(4-methyl-3-oxy-quinazolin-2-yl)methyl]-3-methyl-7-(2-butyn-1-yl)-8-[(R)-3-(tert.-butyloxycarbonylamino)-piperid in-1-yl]-xanthine and 0.59 ml of trifluoroacetic acid in 4 ml of methylene chloride is stirred for one hour at ambient temperature. For working up the reaction mixture is diluted with methylene chloride and water, made alkaline with 1 N sodium hydroxide solution and extracted with methylene chloride. The organic phase is washed with saturated sodium chloride solution, dried over magnesium sulphate and evaporated down. A brownish solid remains.

Yield: 84 mg (84% of theory)
$R_f$ value: 0.50 (reversed phase ready-made TLC plate (E. Merck), acetonitrile/water/trifluoroacetic acid=50:50:1)
Mass spectrum (ESI$^+$): m/z=489 [M+H]$^+$ The following compounds are obtained analogously to Example 1:

(1) 1-[(1-oxy-quinolin-2-yl)methyl]-3-methyl-7-(2-butyn-1-yl)-8-((R)-3-amino-piperidin-1-yl)-xanthine

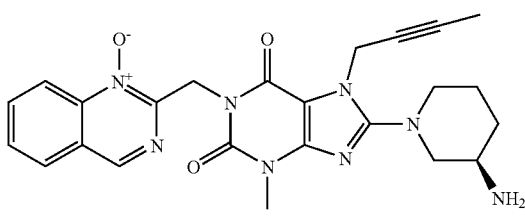

(carried out with isopropanolic hydrochloric acid (5–6 M) in methylene chloride)

$R_f$ value: 0.53 (silica gel, methylene chloride/methanol/conc. aqueous ammonia=90:10:1)

Mass spectrum (ESI⁺): m/z=474 [M+H]⁺

(2) 1-[(3-methyl-2-oxy-isoquinolin-1-yl)methyl]-3-methyl-7-(2-butyn-1-yl)-8-((R)-3-amino-piperidin-1-yl)-xanthine

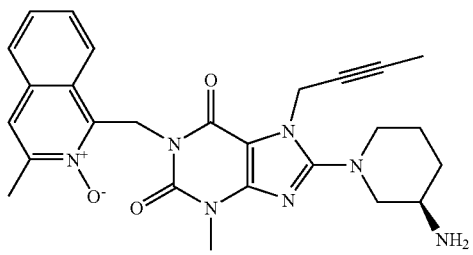

(carried out with isopropanolic hydrochloric acid (5–6 M) in methylene chloride)

$R_f$ value: 0.39 (silica gel, methylene chloride/methanol/conc. aqueous ammonia=90:10:1)

Mass spectrum (ESI⁺): m/z=488 [M+H]⁺

(3) 1-[(5-oxy-phenanthridin-6-yl)methyl]-3-methyl-7-(2-butyn-1-yl)-8-((R)-3-amino-piperidin-1-yl)-xanthine

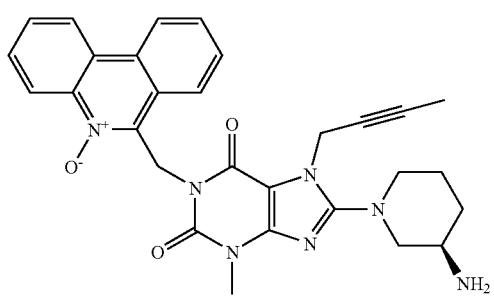

(carried out with isopropanolic hydrochloric acid (5–6 M) in methylene chloride)

$R_f$ value: 0.47 (silica gel, methylene chloride/methanol/conc. aqueous ammonia=90:10:1)

Mass spectrum (ESI⁺): m/z=524 [M+H]⁺

(4) 1-[(3-oxy-quinazolin-2-yl)methyl]-3-methyl-7-(2-butyn-1-yl)-8-((R)-3-amino-piperidin-1-yl)-xanthine

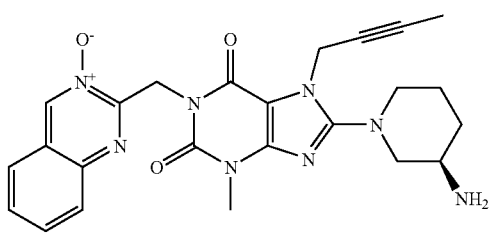

(carried out with isopropanolic hydrochloric acid (5–6 M) in methylene chloride)

$R_f$ value: 0.41 (silica gel, methylene chloride/methanol/conc. aqueous ammonia=90:10:1)

Mass spectrum (ESI⁺): m/z=475 [M+H]⁺

(5) 1-[(1,4-dioxy-quinoxalin-2-yl)methyl]-3-methyl-7-(2-butyn-1-yl)-8-((R)-3-amino-piperidin-1-yl)-xanthine

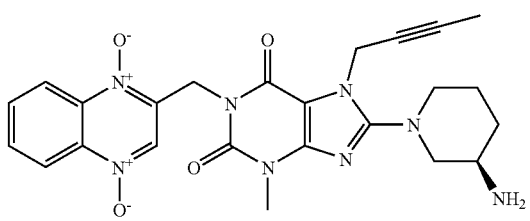

(carried out with isopropanolic hydrochloric acid (5–6 M) in methylene chloride)

$R_f$ value: 0.55 (silica gel, methylene chloride/methanol/conc. aqueous ammonia=90:10:1)

Mass spectrum (ESI⁺): m/z=491 [M+H]⁺

(6) 2-((R)-3-amino-piperidin-1-yl)-3-(2-butyn-1-yl)-5-[(1-oxy-quinolin-2-yl)methyl]-3,5-dihydro-imidazo[4,5-d]pyridazin-4-one

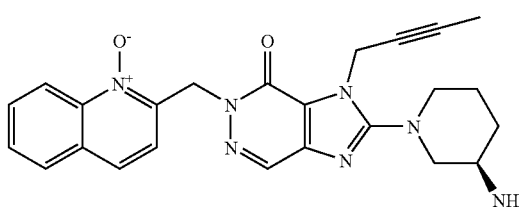

(carried out with isopropanolic hydrochloric acid (5–6 M) in methylene chloride)

R$_f$ value: 0.33 (silica gel, methylene chloride/methanol/conc. aqueous ammonia=90:10:1)
Mass spectrum (ESI$^+$): m/z=444 [M+H]$^+$ (7) 2-((R)-3-amino-piperidin-1-yl)-3-(2-butyn-1-yl)-5-[(3-methyl-2-oxy-isoquinolin-1-yl)methyl]-3,5-dihydro-imidazo[4,5-d]pyridazin-4-one

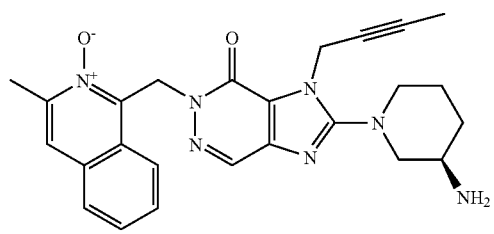

R$_f$ value: 0.27 (silica gel, methylene chloride/methanol/conc. aqueous ammonia=90:10:1)
Mass spectrum (ESI$^+$): m/z=458 [M+H]+

(8) 2-((R)-3-amino-piperidin-1-yl)-3-(2-butyn-1-yl)-5-[(5-oxy-phenanthridin-6-yl)methyl]-3,5-dihydro-imidazo[4,5-d]pyridazin-4-one

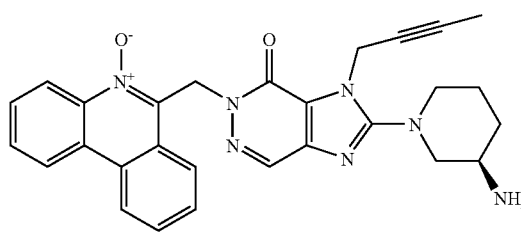

(carried out with isopropanolic hydrochloric acid (5–6 M) in methylene chloride)
R$_f$ value: 0.24 (silica gel, methylene chloride/methanol/conc. aqueous ammonia=90:10:1)
Mass spectrum (ESI$^+$): m/z=494 [M+H]+

(9) 2-((R)-3-amino-piperidin-1-yl)-3-(2-butyn-1-yl)-5-[(3-oxy-quinazolin-2-yl)methyl]-3,5-dihydro-imidazo[4,5-d]pyridazin-4-one

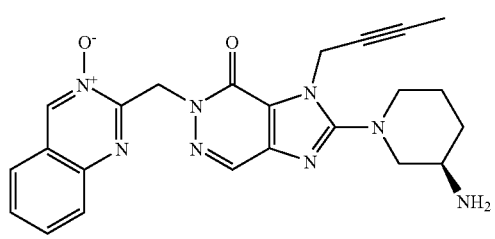

R$_f$ value: 0.24 (silica gel, methylene chloride/methanol/conc. aqueous ammonia=90:10:1)
Mass spectrum (ESI$^+$): m/z=445 [M+H]$^+$

(10) 2-((R)-3-amino-piperidin-1-yl)-3-(2-butyn-1-yl)-5-[(1,4-dioxy-quinoxalin-2-yl)methyl]-3,5-dihydro-imidazo[4,5-d]pyridazin-4-one

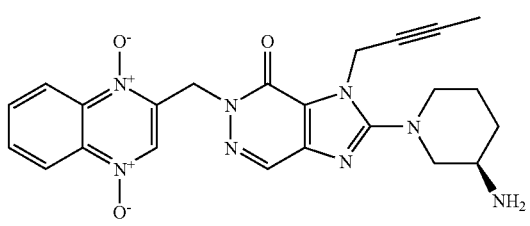

R$_f$ value: 0.26 (silica gel, methylene chloride/methanol/conc. aqueous ammonia=90:10:1)
Mass spectrum (ESI$^+$): m/z=461 [M+H]$^+$

(11) 2-((R)-3-amino-piperidin-1-yl)-3-(2-butyn-1-yl)-5-[(4-methyl-3-oxy-quinazolin-2-yl)methyl]-3,5-dihydro-imidazo[4,5-d]pyridazin-4-one

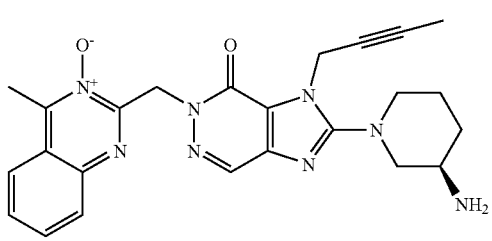

R$_f$ value: 0.60 (reversed phase ready-made TLC plate (E. Merck), acetonitrile/water/trifluoroacetic acid=50:50:1)
Mass spectrum (ESI$^+$): m/z=459 [M+H]$^+$

(12) 1-[(2-oxy-isoquinolin-3-yl)methyl]-3-methyl-7-(2-butyn-1-yl)-8-((R)-3-amino-piperidin-1-yl)-xanthine

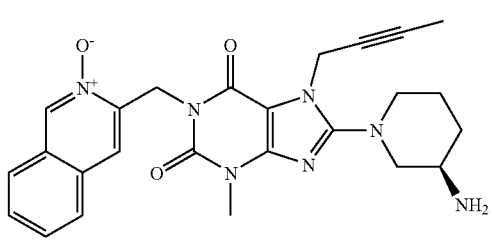

(carried out with isopropanolic hydrochloric acid (5–6 M) in methylene chloride)
R$_f$ value: 0.48 (silica gel, methylene chloride/methanol/conc. aqueous ammonia=90:10:1)
Mass spectrum (ESI$^+$): m/z=474 [M+H]$^+$

(13) 2-((R)-3-amino-piperidin-1-yl)-3-(2-butyn-1-yl)-5-(2-oxy-isoquinolin-3-yl)methyl]-3,5-dihydro-imidazo[4,5-d]pyridazin-4-one

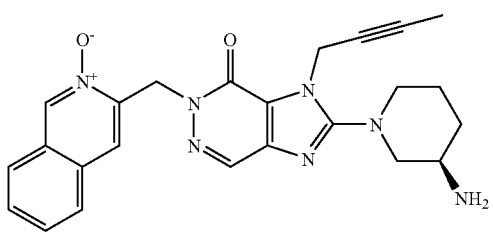

(carried out with isopropanolic hydrochloric acid (5–6 M) in methylene chloride)

$R_f$ value: 0.38 (silica gel, methylene chloride/methanol/conc. aqueous ammonia=90:10:1)

Mass spectrum (ESI$^+$): m/z=444 [M+H]$^+$

EXAMPLE 2

2-(piperazin-1-yl)-3-(2-butyn-1-yl)-5-[(4-methyl-3-oxy-quinazolin-2-yl)methyl]-3,5-dihydro-imidazo[4,5-d]pyridazin-4-one

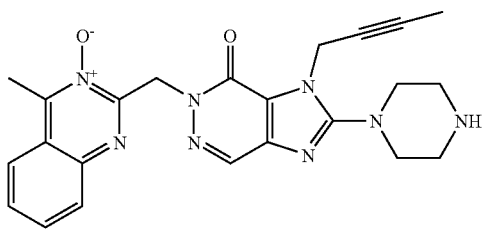

A mixture of 250 mg of 2-bromo-3-(2-butyn-1-yl)-5-[(4-methyl-3-oxy-quinazolin-2-yl)methyl]-3,5-dihydro-imidazo[4,5-d]pyridazin-4-one and 250 mg of piperazine in 5 ml of N,N-dimethylformamide is heated for five minutes in the microwave at 200° C. Then the solvent is distilled off in vacuo and the flask residue is dissolved in methylene chloride. The solution is washed with water and saturated sodium chloride solution and evaporated down in vacuo. The crude product is purified through a silica gel column with methylene chloride/methanol/conc. methanolic ammonia (99:0.9:0.1 to 80:18:2) as eluant.

Yield: 35 mg (14% of theory)

$R_f$ value: 0.60 (silica gel, methylene chloride/methanol/conc. methanolic ammonia=90:9:1)

Mass spectrum (ESI$^+$): m/z=445 [M+H]$^+$

EXAMPLE 3

Coated Tablets Containing 75 Mg of Active Substance

| 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvin-ylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 4

Tablets Containing 100 Mg of Active Substance

Composition:

| 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 5

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 6

Hard Gelatine Capsules Containing 150 mg of Active Substance

| 1 capsule contains: | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 7

Suppositories Containing 150 mg of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 8

Suspension Containing 50 mg of Active Substance

| 100 ml of suspension contain: | | |
|---|---|---|
| active substance | | 1.00 g |
| carboxymethylcellulose-Na-salt | | 0.10 g |
| methyl p-hydroxybenzoate | | 0.05 g |
| propyl p-hydroxybenzoate | | 0.01 g |
| glucose | | 10.00 g |
| glycerol | | 5.00 g |
| 70% sorbitol solution | | 20.00 g |
| flavouring | | 0.30 g |
| dist. water | ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 9

Ampoules Containing 10 mg Active Substance

| Composition: | | |
|---|---|---|
| active substance | | 10.0 mg |
| 0.01 N hydrochloric acid q.s. | | |
| double-distilled water | ad | 2.0 ml |

Preparation:

The active substance is dissolved in the necessary amount of 0.01 N HCl, made isotonic with common salt, filtered sterile and transferred into 2 ml ampoules.

EXAMPLE 10

Ampoules Containing 50 mg of Active Substance

| Composition: | | |
|---|---|---|
| active substance | | 50.0 mg |
| 0.01 N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

What is claimed is:

1. Compounds of general formula

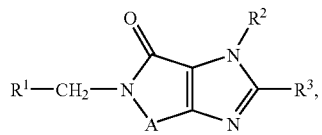

wherein $R^1$ denotes a pyridinyl, phenylpyridinyl, (pyridinylphenyl)carbonyl, quinolinyl, phenylquinolinyl, isoquinolinyl, phenylisoquinolinyl, phenanthridinyl, pyridazinyl, phenylpyridazinyl, (pyridazinylphenyl)carbonyl, pyrimidinyl, phenylpyrimidinyl, (pyrimidinylphenyl)carbonyl, (pyrazinylphenyl)carbonyl, quinolinyl, phenylquinolinyl, quinazolinyl, phenylquinazolinyl, phthalazinyl, phenyl -phthalazinyl, quinoxalinyl, phenylquinoxalinyl, naphthyridinyl or phenylnaphthyridinyl substituted by the groups $R^{10}$ to $R^{12}$, while at least one nitrogen atom of the above-mentioned groups is substituted by an oxygen atom, and $R^{10}$ denotes hydrogen, fluorine, chlorine, bromine, or iodine, $C_{1-4}$-alkyl, hydroxyl, $C_{1-4}$-alkyloxy, nitro, amino, $C_{1-3}$-alkylamino, di-($C_{1-3}$-alkyl)amino, pyrrolidin-1-yl, piperidin-1-yl, morpholin-4-yl, $C_{1-3}$-alkyl-carbonylamino, N—($C_{1-3}$-alkyl)—$C_{1-3}$-alkyl-carbonylamino, $C_{1-3}$-alkylsulphonylamino, N—($C_{1-3}$-alkyl)—$C_{1-3}$-alkylsulphonylamino, $C_{1-3}$-alkyl-carbonyl, cyano, aminocarbonyl, ($C_{1-3}$-alkylamino)carbonyl, [di-($C_{1-3}$-alkyl)amino]carbonyl, pyrrolidin-1-ylcarbonyl, piperidin-1-ylcarbonyl, morpholin-4-ylcarbonyl, methyl, methoxy substituted by 1 to 3 fluorine atoms, $C_{1-3}$-alkylsulphanyl, $C_{1-3}$-alkylsulphinyl, $C_{1-3}$-alkylsulphonyl, $C_{2-4}$-alkenyl, $C_{2-4}$-alkynyl group, $C_{3-4}$-alkenyloxy, $C_{3-4}$-alkynyloxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, aryl, aryloxy, aryl-$C_{1-3}$-alkyl, or aryl-$C_{1-3}$-alkyloxy, and $R^{11}$ and $R^{12}$, which may be identical or different, represent hydrogen, fluorine, chlorine, bromine, methyl, difluoromethyl, trifluoromethyl, methoxy, difluoromethoxy, trifluoromethoxy, or cyano, $R^2$ denotes 2-methyl-2-propen-1-yl, 2-chloro-2-propen-1-yl, or 3-bromo-2-propen-1-yl, 1-buten-1-yl, 3-methyl-1-buten-1-yl, 3-methyl-2-buten-1-yl, 2-buten-1-yl, 2-methyl-2-buten-1-yl, 2,3-dimethyl-2-buten-1-yl, 2-butyn-1-yl, 1-cyclopenten-1-ylmethyl, benzyl, 2-fluorobenzyl, 2-chlorobenzyl, 2-bromobenzyl-, or 2-cyanobenzyl, $R^3$ denotes 3-aminopiperidin-1-yl, 3-amino-azepan-1-yl, piperazin-1-yl, [1,4]-diazepan-1-yl, or an amino group substituted by the groups $R^4$ and $R^5$, wherein $R^4$ denotes a methyl or ethyl group and $R^5$ denotes a 2-aminoethyl group, while the ethyl moiety of the 2-aminoethyl group may be substituted by one or two methyl groups, A denotes a —CO—N($R^6$)— group, while the nitrogen atom of this group is linked to the imidazo ring of general formula I, and $R^6$ denotes hydrogen, $C_{1-4}$-alkyl, $C_{3-6}$-cycloalkyl, or an aryl group, or A denotes —CH=CH— substituted by $R^6$, where $R^6$ is as hereinbefore defined, or A denotes —C($R^7$)=N—, where the nitrogen atom of this group is linked to the imidazo ring of general formula I, and $R^7$ denotes hydrogen, $C_{1-4}$-alkyl, $C_{3-6}$-cycloalkyl, or an aryl group, or A denotes —N=C($R^7$), while the carbon atom of this group is linked to the imidazo ring of general formula I, and $R^7$ is as hereinbefore defined, while by the aryl groups mentioned in the definition of the above groups is meant a phenyl group substituted by $R^{10}$ and $R^{11}$ as hereinbefore defined, and the above-mentioned alkyl and alkenyl groups may be straight-chain or branched, the tautomers, the enantiomers, the diastereomers, the mixtures thereof and the salts thereof.

2. Compounds of general formula I according to claim 1, wherein $R^1$ denotes a pyridinyl, phenylpyridinyl, (pyridinylphenyl)carbonyl, quinolinyl, phenylquinolinyl, isoquinolinyl, phenylisoquinolinyl, phenanthridinyl, pyrimidinyl, phenylpyrimidinyl, (pyrimidinylphenyl)carbonyl, quinazolinyl, phenylquinazolinyl, quinoxalinyl, phenylquinoxalinyl, or naphthyridinyl substituted by the groups $R^{10}$ and $R^{11}$, while at least one nitrogen atom of the above-mentioned groups is substituted by oxygen, and $R^{10}$ and $R^{11}$, which may be identical or different, denote hydrogen, fluorine, chlorine, bromine, methyl, difluoromethyl, trifluoromethyl, methoxy, difluoromethoxy, trifluoromethoxy, or cyano, $R^2$ denotes a 2-butyn-1-yl group, $R^3$ denotes a 3-aminopiperidin-1-yl, piperazin-1-yl or [1,4]-diazepan-1-yl group, or an amino group substituted by the groups $R^4$ and $R^5$, wherein $R^4$ denotes methyl or ethyl, and $R^5$ denotes 2-aminoethyl, while the ethyl moiety of the 2-aminoethyl group may be substituted by one or two methyl groups, A denotes —CO—N($R^6$)—, while the nitrogen atom of this group is linked to the imidazo ring of general formula I, and $R^6$ denotes methyl, ethyl, propyl, isopropyl, cyclopropyl, or phenyl, or A denotes —N=C($R^7$)—, while the carbon atom of this group is linked to the imidazo ring of general formula I, and $R^7$ denotes hydrogen or methyl, the tautomers, the enantiomers, the diastereomers, the mixtures thereof and the salts thereof.

3. Compounds of general formula I according to claim 1, wherein $R^1$ denotes a phenylpyridinyl, quinolinyl, isoquinolinyl, phenanthridinyl, phenylpyrimidinyl, quinazolinyl, quinoxalinyl, or naphthyridinyl substituted by the groups $R^{10}$ and $R^{11}$, while the nitrogen atom of the above-mentioned groups is substituted by an oxygen atom, and $R^{10}$ denotes hydrogen, methyl, methoxy, or cyano, and $R^{11}$ denotes hydrogen or methyl, $R^2$ denotes 2-butyn-1-yl, $R^3$ denotes 3-aminopiperidin-1-yl, piperazin-1-yl, or [1,4]-diazepan-1-yl group, or an amino group substituted by the groups $R^4$ and $R^5$, wherein $R^4$ denotes methyl and $R^5$ denotes 2-aminoethyl, while the ethyl moiety of the 2-aminoethyl group may be substituted by one or two methyl groups, A denotes —CO—N($R^6$)—, while the nitrogen atom of this group is linked to the imidazo ring of general formula I, and $R^6$ denotes methyl, ethyl, isopropyl, cyclopropyl, or phenyl, or A denotes —N=C($R^7$)—, while the carbon atom of this group is linked to the imidazo ring of general formula I, and $R^7$ denotes hydrogen or methyl, the tautomers, the enantiomers, the diastereomers, the mixtures thereof and the salts thereof.

4. Compounds according to general formula 1 of claim 1 wherein $R^3$ denotes 3-aminopiperidin-1-yl, the tautomers, the enantiomers, the diastereomers, the mixtures thereof and the salts thereof.

5. Compounds according to general formula 1 of claim 1, wherein $R^3$ denotes piperazin-1-yl, the tautomers, the enantiomers, the diastereomers, the mixtures thereof and the salts thereof.

6. Compounds according to general formula 1 of claim 1, wherein $R^3$ denotes [1,4]-diazepan-1-yl, the tautomers, the enantiomers, the diastereomers, the mixtures thereof and the salts thereof.

7. Compounds of general formula I according to claim 1, wherein $R^1$ is chosen from quinolinyl, isoquinolinyl, methylisoquinolinyl, phenanthridinyl, quinazolinyl, or methyiquinazolinyl, while the nitrogen atom of the above-mentioned groups is substituted by an oxygen atom, or a quinoxalinyl, wherein both nitrogen atoms are substituted by oxygen atoms, $R^2$ denotes 2-butyn-1-yl, $R^3$ denotes 3-aminopiperidin-1-yl or piperazin-1-yl, A denotes —CO—N($R^6$)—, while the nitrogen atom of this group is linked to the imidazo ring of general formula I, and $R^6$ denotes a methyl group, or A denotes —N=C($R^7$)—, while the carbon atom of this group is linked to the imidazo ring of general formula I, and $R^7$ denotes hydrogen, the tautomers, the enantiomers, the diastereomers, the mixtures thereof and the salts thereof.

8. The following compounds of general formula I according to claim 1 chosen from:
  (a) 1-[(4-methyl-3-oxy-quinazolin-2-yl)methyl]-3-methyl-7-(2-butyn-1-yl)-8-((R)-3-amino-piperidin-1-yl)-xanthine,
  (b) 1-[(1-oxy-quinolin-2-yl)methyl]-3-methyl-7-(2-butyn-1-yl)-8-((R)-3-amino-piperidin-1-yl)-xanthine,
  (c) 1-[(3-methyl-2-oxy-isoquinolin-1-yl)methyl]-3-methyl-7-(2-butyn-1-yl)-8-((R)-3-amino-piperidin-1-yl)-xanthine,
  (d) 1-[(5-oxy-phenanthridin-6-yl)methyl]-3-methyl-7-(2-butyn-1-yl)-8-((R)-3-amino-piperidin-1-yl)-xanthine,
  (e) 1-[(3-oxy-quinazolin-2-yl)methyl]-3-methyl-7-(2-butyn-1-yl)-8-((R)-3-amino-piperidin-1-yl)-xanthine,
  (f) 2-((R)-3-amino-piperidin-1-yl)-3-(2-butyn-1-yl)-5-[(1-oxy-quinolin-2-yl)methyl)]-3,5-dihydro-imidazo[4,5-d]pyridazin-4-one,
  (g) 2-((R)-3-amino-piperidin-1-yl)-3-(2-butyn-1-yl)-5-[(3-oxy-quinazolin-2-yl)methyl]-3,5-dihydro-imidazo[4,5-d]pyridazin-4-one,
  (h) 2-(piperazin-1-yl)-3-(2-butyn-1-yl)-5-[(4-methyl-3-oxy-quinazolin-2-yl)methyl]-3,5-dihydro-imidazo[4,5-d]pyridazin-4-one,
  (i) 2-((R)-3-amino-piperidin-1-yl)-3-(2-butyn-1-yl)-5-[(4-methyl-3-oxy-quinazolin-2-yl)methyl]-3,5-dihydro-imidazo[4,5-d]pyridazin-4-one,
  (j) 1-[(2-oxy-isoquinolin-3-yl)methyl]-3-methyl-7-(2-butyn-1-yl)-8-((R)-3-amino-piperidin-1-yl)-xanthine and
  (k) 2-((R)-3-amino-piperidin-1-yl)-3-(2-butyn-1 -yl)-5-(2-oxy-isoquinolin-3-yl)methyl]-3,5-dihydro-imidazo[4,5-d]pyridazin-4-one as well as the tautomers, the enantiomers, the diastereomers, the mixtures thereof and the salts thereof.

9. Physiologically acceptable salts of the compounds of general formula I according to claim 1 with inorganic or organic acids.

10. A pharmaceutical composition comprised of a compound of general formula I according to claim 1 or a physiologically acceptable salt thereof optionally together with one or more inert carriers and or diluents.

11. A method of treating a disease, disorder, or condition chosen from type I and II diabetes mellitus, obesity, and calcitonin-induced osteoporosis comprised of the steps of administering to a patient in need therof a therapeutically effective amount of a compound of general formula I according to claim 1.

12. Process for preparing a pharmaceutical composition of general formula I according to claim 1, comprised of the steps of incorporating said compound into one or more inert carriers and/or diluents by a non-chemical method.

13. Process for preparing the compounds of general formula I according to claim 1, comprised of the step of reacting a compound of general formula

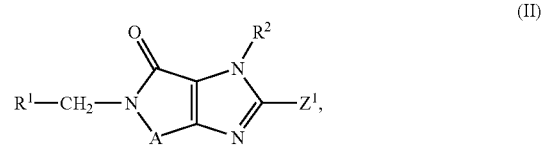

(II)

wherein $R^1$, $R^2$ and A are defined as mentioned in claim 1 and $Z^1$ denotes a leaving group such as a halogen atom, a substituted hydroxy, mercapto, sulphinyl, sulphonyl or sulphonyloxy group, with $R^3$-H, the enantiomers or the salts thereof, where $R^3$ is as hereinbefore defined.

14. Process for preparing the compounds of general formula I according to claim 1, comprised of the step of deprotecting a compound of general formula

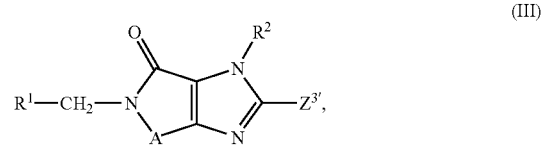

(III)

wherein $R^1$, $R^2$ and A are defined as defined in claim 1, and $R^{3'}$ denotes one of the groups mentioned in the definition of $R^3$ hereinbefore wherein the amino or imino group is protected by a protecting group;

and optionally cleaving any protecting groups used during the reaction;

and optionally resolving the compounds of general formula I thus obtained are into their enantiomers and/or diastereomers;

and optionally converting the compounds of general formula I into physiologically acceptable salts thereof with inorganic or organic acids.

* * * * *